United States Patent [19]
Josephson et al.

[11] Patent Number: 5,160,726
[45] Date of Patent: Nov. 3, 1992

[54] FILTER STERILIZATION FOR PRODUCTION OF COLLOIDAL, SUPERPARAMAGNETIC MR CONTRAST AGENTS

[75] Inventors: Lee Josephson, Arlington; Ernest V. Groman, Brookline; Stephen Palmacci, Walpole, all of Mass.

[73] Assignee: Advanced Magnetics Inc., Cambridge, Mass.

[21] Appl. No.: 650,957

[22] Filed: Feb. 5, 1991

Related U.S. Application Data

[63] Continuation-in-part of Ser. No. 480,677, Feb. 15, 1990, abandoned.

[51] Int. Cl.$^5$ .................. G01N 24/00; G01N 31/00; A61K 33/26; A61K 31/715
[52] U.S. Cl. ...................... 424/9; 424/646; 424/648; 436/173; 436/806; 128/653.4; 514/59; 514/836
[58] Field of Search ............ 424/9, 646, 648; 436/173, 806; 128/653 CA, 653 AF, 654; 514/59, 836

[56] References Cited

U.S. PATENT DOCUMENTS

| | | | |
|---|---|---|---|
| 2,820,740 | 1/1958 | London et al. | 167/68 |
| 3,536,696 | 10/1970 | Alsop et al. | 260/209 |
| 4,101,435 | 7/1978 | Hasegawa et al. | 252/62.53 |
| 4,501,726 | 2/1985 | Schroder et al. | 424/1.1 |
| 4,554,088 | 11/1985 | Whitehead et al. | 252/62.54 |
| 4,770,183 | 9/1988 | Groman et al. | 128/654 |
| 4,795,698 | 1/1989 | Owen et al. | 435/4 |
| 4,827,945 | 5/1989 | Groman et al. | 128/653 |
| 4,863,715 | 9/1989 | Jacobsen et al. | 424/9 |

FOREIGN PATENT DOCUMENTS 248524 12/1987 European Pat. Off. .

OTHER PUBLICATIONS

Akers, M. J. (1984) Pharm. Tech., May pp. 36–45.
Hemmingsson et al. (1987) Acta Radiologica 28 pp. 703–705.
Josephson et al. (1990) Magnetic Resonance Imaging 8 pp. 637–646.
McClennan, B. L. (1987) Radiology 162 pp. 1–8.
Saini et al. (1987) Radiology 162 pp. 211–216.
Stark et al. (1988) Radiology 168 pp. 297–301.
Weissleder et al. (1989) Amer. J. Roent. 152 pp. 167–173.
Widder et al. (1987) Amer. J. Roent. 148 pp. 399–404.
Williams and Polli (1984) J. Parenteral Science and Technology 38 pp. 48–59.
J. T. Ferucci and D. D. Stark (1990) AJR 155: 943–950.
R. D. Hamstra et al. (1980) JAMA 243 pp. 1746–1731.

*Primary Examiner*—Richard L. Raymond
*Assistant Examiner*—Gary E. Hollinden
*Attorney, Agent, or Firm*—Bromberg & Sunstein

[57] ABSTRACT

An improvement is provided to a method for obtaining an in vivo MR image of an organ or tissue of an animal or human subject, of the type including administering to the subject as a contrast agent to enhance such MR image an effective amount of a colloid including superparamagnetic metal oxide particles dispersed in a physiologically acceptable carrier. In accordance with the improvement, the method includes preparing the colloid in a manner that provides a reduction in toxicity in comparison with that associated with administration of the colloid after terminal sterilization. The improvement may include sterilizing the colloid by filtration. In an additional embodiment, the colloid may be sterilized by filtration and preserved by lyophilization. The colloid may be lyophilized in the presence of a compatible excipient. The excipient utilized may include a dextran or a citrate anion. Other embodiments include related compositions and methods.

20 Claims, 3 Drawing Sheets

FILTER STERILIZATION FOR PRODUCTION OF COLLOIDAL, SUPERPARAMAGNETIC MR CONTRAST AGENTS

CROSS REFERENCE TO RELATED APPLICATIONS

This is a continuation-in-part of application Ser. No. 0,677, filed on Feb. 15, 1990 now abandoned. This related application is hereby incorporated herein by reference.

FIELD OF INVENTION

The present invention relates generally to magnetic resonance (MR) contrast agents and their preparation, and particularly to sterilization for production of such agents.

BACKGROUND OF THE INVENTION

A. The Need to Manufacture MR Contrast Agents Exhibiting the Lowest Possible Rates of Adverse Reactions The efficacy of superparamagnetic colloids as parenteral, MR contrast agents (U.S. Pat. No. 4,827,945; U.S. Pat. 4,770,183; Stark et al. Radiology 168:297-301 (1988); Hemmingsson et al. Acta Radiologica 28:703-705 (1987)) has generated the need to produce these materials in sterile form, with the lowest possible incidence of (or degree of) adverse reactions resulting from their injection. (The foregoing two United States patents are hereby incorporated herein by reference.) An adverse reaction is an undesirable physiological response, sensation or symptom that occurs after the injection of a contrast agent. Examples of adverse reactions include blood pressure alterations, hives, vomiting and headache (see Dean, P.B. and Paajanen, H. "Undesirable Consequence of Intravascular Contrast Media Administration" in Contrast Media: Bioloqical Effects and Clinical Aoolication. (Parvez, Z., Moncada, R. and Sovak, M. eds., (CRC Press, Boca Raton, FL) vol. I, pp. 69-75). The commercial value of superparamagnetic colloids as parenteral MR contrast agents depends not only on the efficacy of a particular active ingredient, and the lack of acute toxicity, but on the ability to manufacture that ingredient in a manner consistent with stringent sterility requirements on the one hand, while producing the lowest possible incidence of (or degree of) adverse reactions on the other hand.

The need to minimize adverse reactions for MR contrast agents involves two considerations. First, governmental agencies regulating the sale of pharmaceuticals must be convinced that the incidence (or degree of) of adverse reactions is sufficiently low to permit the manufacturer to sell the agent. Second, within the competitive commercial marketplace, the relative incidence of adverse reactions exhibited by various agents, each approved for sale and each having a similar medical use, can determine the market share (or price obtained) for each agent. Each of these factors is discussed further below.

The need for contrast media to exhibit a very low incidence of adverse reactions in order to be approved by government agencies regulating their sale reflects the fact that such agents may be administered to individuals suspected of, but in fact free of, disease. Therapeutic agents are generally given to a population exhibiting some pathological condition, and those individuals benefit from the administration of the agent. With therapeutic agents a larger degree of adverse reactions may be to tolerated. For example, many of the agents used in cancer chemotherapy cause a number of adverse reactions or side effects.

Even when contrast media are sufficiently safe for regulatory agencies to approve their use in humans, the relative incidence of adverse reactions obtained with competing products can affect the market share, or price obtained for specific agents. For example, so-called nonionic angiographic contrast media have been developed and marketed as superior to ionic contrast media because the former, though more expensive, are believed to exhibit lower rates of adverse reactions (McClennan, B.L. Radiology 62:1-8 (1987)). In the marketplace of diagnostic contrast media, the ability to minimize even low rates of adverse reactions (e.g. reactions in 0.01-10.0% of those persons injected), can strengthen the commercial position of one product relative to another.

B. Methods of Sterilization for Parenteral Agents

For a pharmaceutical, the degree of sterility assurance needed and the sterilization method selected depends in large measure on the route of administration. Parenterally administered agents are those administered through the skin including by the intravenous, subcutaneous or intraperitoneal modes of administration. Sterility requirements are most stringent for agents administered through the skin and introduced into a sterile environment of the body. There are only two widely recognized methods for sterilizing solutions for parenteral administration. The first method (filter sterilization) involves passing a solution through a 0.22 micron filter (220 nm). The second method (so-called terminal sterilization) involves the use of heat, typically 121 ° C. for 30 minutes. The current use of 0.22 micron filtration to achieve sterility, instead of 0.45 micron filtration, which was earlier seen as sufficient, reflects recent studies that some bacteria are small enough to pass through 0.45 micron filters.

It is known that some MR contrast agents may be filtered through filters of the order of 0.2 microns U.S. Pat. Nos. 4,770,183 (col. 12, lines 59-61), 4,827,945 (col. 17 lines 51-53), and 4,795,698 (col. 3, lines 55-57), and thus may be filter sterilized. However, for the reasons discussed below, filter sterilization is not favored. Moreover, although filterability of MR contrast agents may be achieved by prior art methods, yields of such materials are often unacceptably low or inefficient on account, for example, of filter clogging and other difficulties.

On the basis of sterility assurance, terminal sterilization is preferred over filter sterilization by regulatory agencies. Filter sterilization has a failure rate resulting from the fact that a sterile solution must be added to a sterile vial and the vial sealed under sterile conditions. Terminal sterilization offers a higher degree of sterility assurance than filter sterilization. With terminal sterilization, heat sterilization occurs within a closed container, which is not opened until it reaches the user. Filter sterilization has a low but inescapable probability of failure due to contamination from air borne microorganisms during the bottling process. When manufacturing a large number of vials, the low sterilization failure rate will result in a considerable number of nonsterile vials. Initially the number of microorganisms in these nonsterile vials is low and considered safe for injection.

Depending on the time, temperature and the storage media, the few microorganisms present in these nonsterile vials may increase, which would produce severe reactions, if injected.

The preference for terminal sterilization, wherever an active ingredient might withstand heat stress, has increased in recent years. This is due to increasingly costly and complex liability issues that can confront the manufacturer of an occasional nonsterile vial. In addition, government agencies responsible for regulating pharmaceutical manufacture have a tendency to increase over time the standards of safety, quality, and product uniformity required of the manufacturer. Terminal sterilization appears to be particularly desirable for parenteral administered superparamagnetic iron oxide colloids because the highly colored nature of the iron prevents visual inspection, which might otherwise be used to detect vials grossly contaminated with microorganisms. Visual inspection can be used to detect colonies of microorganisms in clear, filter sterilized solutions.

Terminal sterilization has been used with iron oxide colloids of various types, and the resulting compounds are widely believed to have excellent toxicological properties. For example, the paramagnetic iron-dextran used in the treatment of anemia has an intravenous $LD_{50}$ of at least 800 mg/kg with a 30 minute autoclaving (see example 1 of U.S. Pat. No. 2,820,740.) (Note: We report the mass of iron in the manner cited in the publication or patent, in either mg Fe or $\mu$moles Fe. One mg Fe is equivalent to about 20 $\mu$moles of iron.) Similar results have been reported with dextran iron oxide where an autoclaved preparation had an $LD_{50}$ in mice of greater than 3,800 mg Fe/kg (see example 1 of U.S. Pat. 3,536,696). Dextran magnetite has been reported to have an $LD_{50}$ of 4100 mg Fe/Kg of body weight (example 1 of U.S. Pat. No. 4,101,435, which patent is hereby incorporated herein by reference). The compound is supplied by the assignee as sol pasteurized for 15 minutes at 110 °C. Finally, the citrate stabilized biodegradable, superparamagnetic colloids can be autoclaved with retention of their physical state (see example 7.9 of U.S. Pat. 4,827,945). This citrate stabilized superparamagnetic iron oxide has an $LD_{50}$ of at least 3000 $\mu$moles Fe/Kg in rodents (Weissleder et al. Amer. J. Roent. 152: 167–173 (1989)), and an overall toxicological profile that has been safe enough to permit human clinical studies (Stark et al, Radiology 168:297–301 (1988).

The preference for terminal sterilization over filter sterilization on the basis of sterility assurance, the generally low acute toxicity observed with terminally sterilized iron oxide preparations, and the difficulty of visually detecting microbial contamination, all combine to suggest that terminal sterilization is the method of choice for parenteral superparamagnetic iron oxide colloids.

SUMMARY OF THE INVENTION

This invention concerns the recognition of a previously unrecognized problem involving the safety of materials used as MR contrast agents. The current invention involves the surprising observation that terminal sterilization can modify superparamagnetic iron oxide colloids so that a drop in blood pressure (a highly undesirable adverse reaction) is more likely to result from their administration. The observation is surprising because terminally sterilized iron oxide colloids of various types have very low acute toxicities in rodents (or other animals) and have been considered to have excellent toxicological properties generally. The acute toxicity of a compound is often taken as indicating the overall toxicity of a material. In addition, terminal sterilization is generally preferred as a sterilization method for parenterals because it has the lowest probability yielding nonsterile containers. When terminal sterilization is replaced by filter sterilization the drop in blood pressure resulting from the injection of the colloid is eliminated. Processes for the manufacture of superparamagnetic iron oxide colloids where filter sterilization is used are the subject of the current invention.

In accordance with the present invention, a colloid including superparamagnetic metal oxide particles dispersed in a physiologically acceptable carrier is prepared in a manner that provides a reduction in toxicity in comparison with that associated with administration of the colloid after terminal sterilization. In accordance with the invention, the colloid may be sterilized by filtration. The colloid may also be preserved by lyophilization and an excipient, such as a dextran or a citrate anion, may be included during the lyophilization.

BRIEF DESCRIPTION OF THE DRAWINGS

The foregoing features of the invention will be more readily understood by reference to the following detailed description, taken with the accompanying drawings, in which.

DETAILED DESCRIPTION OF SPECIFIC EMBODIMENTS

Figure 1:
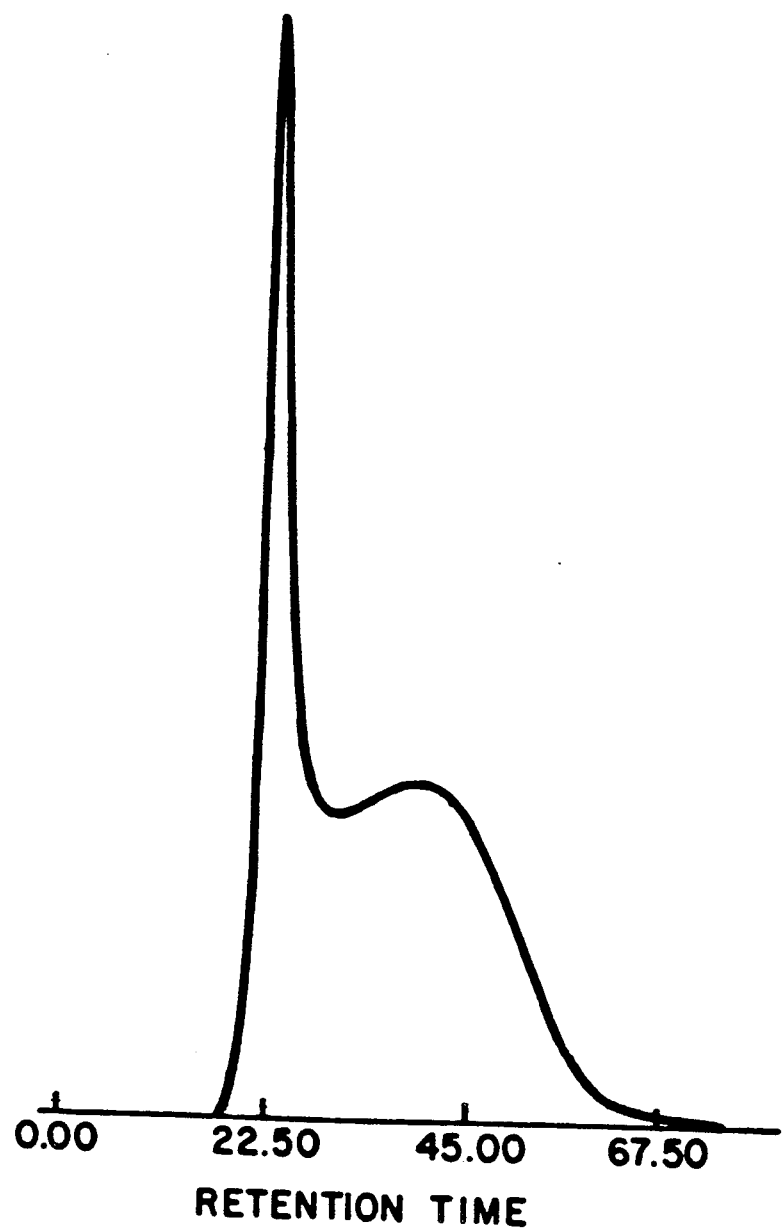
FIG. 1 is a Sepharose 4B chromatogram of superparamagnetic iron oxide colloid, never lyophilized, in accordance with Example 4.

A. Size Range of Active Ingredients Covered by the Invention

Active ingredients applicable to the current invention include colloidal superparamagnetic metal oxides, including those of iron, cobalt and manganese. The invention is equally applicable to colloids in which the metal oxide particles are associated with macromolecular substances. Such active ingredients include but are not limited to the compositions described in U.S. Pat. Nos. 4,827,945; 4,770,183; 4,101,435; 4,795,698; 4,863,715; and 4,501,726; which patents are hereby incorporated herein by reference.

Superparamagnetic compounds have a high magnetic moment (e.g. 5–90 EMU/gm iron oxide) in the presence of a magnetic field but retain no magnetic moment in the absence of a magnetic field. By "colloidal" is meant a material that (1) does not settle out of solution on standing, (2) cannot be recovered with conventional filtration techniques, and (3) has a negligible or low osmotic pressure. Superparamagnetic iron oxides achieve these three properties when they are within the size range of about 5 to 500 nm as measured by laser light scattering. Larger materials, materials in micron size range, settle out of solution on standing and are referred to as particulate rather than colloidal. An additional general characteristic of magnetic particles is that they can be promptly withdrawn from solution by a hand magnet.

To be subject to the process of the invention, i.e. to be filter sterilized, a superparamagnetic colloid must be able to pass through a 0.22 micron (220 nm) filter. This requirement is met when (1) the size of an average particle is below 220 nm and (2) the colloid is homogeneous with respect to size and therefore free of all material of about 220 nm or larger that might clog the filter.

Typical magnetic particles (i.e. materials in the micron size range) cannot pass through a 0.22 micron filter because of their large average particle size. Magnetic particles have proven efficacious as MR contrast agents, including micron size silanized clusters (Saini et al. Radiology 162: 211-216 (1987)), 0.5 micron starch matrix particles (Hemmingsson et al. Acta Radiologica 28:703-705 (1987), and a 1-5 micron sized albumin microspheres (Widder et al. Amer. J. Roent. 148:399-404 (1987)).

Due to a lack of size homogeneity, many superparamagnetic iron oxide colloids cannot easily pass through a 220 nm filter, even though their median or mean size in solution is below 220 nm. For example, the superparamagnetic colloid made according to example 7.10 of U.S. Pat. No. 4,827,945 has a volume median diameter by light scattering of between 50 and 100 nm. This colloid cannot be 220 nm filter sterilized due to the presence of a small amount of material that is about 220 nm or greater in size and this material clogs the filter. Removal of the larger materials by centrifugation permits this superparamagnetic iron oxide colloid to become filterable. (See example 3 below.) The ability to pass through a 220 nm filter is a requirement not met by many materials that have been used as MR contrast agents.

B. Examples: Methods of Preparing Filter Sterilizable, Superparamagnetic Iron Oxide Colloids There are two general ways of making filter sterilizable superparamagnetic colloids. The first is by direct synthesis of a colloid having a sufficiently small average size to permit filter sterilization. The second, size fractionation, can be employed when colloids have an average size that would seem to permit filter sterilization (i.e. well below 220 nm), but clog the filter when 220 nm filtration is attempted. In this case materials of about 220 nm or larger can be removed from the colloid, and 220 nm filtration can be accomplished. There are at least four commercially practical separation methods for removing the larger materials that block the filter sterilization of superparamagnetic colloids. They are:

(1) Filtration through progressively smaller pore size filters, culminating with a 220 nm filtration for sterility.

(2) Magnetic filtration, where larger particles are selectively removed by attraction to a magnetized grid known as a magnetic filter.

(3) Column chromatography, particularly gel permeation chromatography, that removes particles above a certain size by the usual principles of gel chromatography.

(4) Centrifugation, where larger particles are precipitated and discarded and the supernatant is then filtered.

The methods above can be used in combination with each other or with other fractionation or separation methods.

EXAMPLE 1: DIRECT SYNTHESIS OF A FILTER STERILIZABLE SUPERPARAMAGNETIC COLLOID USING DEXTRAN

To an aqueous solution (250 mL) of $FeCl_3.6H_2O$ (35g) and $FeCl_2.4H_2O$ (16g) is added a sufficient amount of aqueous sodium carbonate to bring the pH of the solution to about 2.3. Solid dextran (150g) is then added. The solution is stirred and heated to about 60°-70° C. for about 15 minutes and allowed to cool to 40°-45° C. To the reddish solution is added 7.5% $NH_4OH$ to yield a pH of between 9.5 and 10. A greenish suspension is produced which is subsequently heated to 95°-100° C. for 15 minutes. (It should be noted that the application of heat as part of the process in this and subsequent examples does not satisfy generally accepted standards for terminal sterilization, and that the approach of the present invention is generally required for sterilization in the absence of terminal sterilization.) The resulting black suspension is put through an ultrafiltration step using an Amicon RA 2000 hollow fiber dialysis unit equipped with a cartridge having a nominal cutoff of 100 kilodaltons. Light scattering measurements reveal the resulting particle has a volume median diameter of about 40 nm.

EXAMPLE 2: SYNTHESIS OF A FILTER STERILIZABLE SUPERPARAMAGNETIC COLLOID USING THE CARBOHYDRATE ARABINOGALACTAN

An aqueous solution of trivalent and divalent metal salts is prepared by the use of the following amounts of ferric and ferrous halide salts: $FeCl_3.6H_2O$ (15.8 g, 58.5 mmol) and $FeCl_2.4H_2O$ (6.24 g, 31.6 mmol) and combined in distilled water (200 mL) and the resulting solution is filtered through a 0.22 $\mu$m glass fiber filter to remove large debris. Equal volumes of this metal halide solution and a carbohydrate solution, prepared by dissolving arabinogalactan from larch wood (60 g, Sigma Chemical Co.) in 120 mL, are then combined at ambient temperature with vigorous stirring. To this is then added slowly and dropwise, a 30% aqueous ammonium hydroxide solution until the pH of the mixture reaches about 10. At this stage, the mixture is heated to 90°-100° C. for about 15 minutes. The mixture is allowed to cool with the formation of a black, colloidal, superparamagnetic iron oxide. The cooled mixture is then passed through a coarse glass filter, followed by a series of filters of decreasing porosity beginning with 0.8 $\mu$m, then using a 0.45 $\mu$m and finally an 0.22 $\mu$m filter.

Excess arabinogalactan is removed by ultrafiltration using a 2 liter hollow fiber dialysis unit having a 300 kilodalton molecular weight cutoff (Amicon Inc., Danvers, MA) as follows: the filtered product from the preceding step is loaded into the ultrafiltration unit, and diluted and washed with 25 mM sodium citrate buffer (pH 8.5). This washing step is repeated until a clear eluent is observed (about 5 cycles). The washed product is then concentrated to a final volume which is about equal to the initial volume of combined metal and carbohydrate solutions. The product can be filter sterilized by passage through a 0.22 $\mu$m filter and stored at 2-8° C. until needed.

EXAMPLE 3: PREPARATION OF A FILTER STERILIZABLE SUPERPARAMAGNETIC COLLOID BY CENTRIFUGATION

A superparamagnetic iron oxide colloid was made according to example 7.10 of U.S. Pat. No. 4,827,945. After ultrafiltration the colloid cannot be filter sterilized, though as indicated in the patent citrate can be added and the colloid autoclaved. The ultrafiltered colloid (but unautoclaved colloid) was obtained at 100 mg/mL Fe and was centrifuged for 30 minutes at 30,000× gravity. The pellet discarded. The supernatant colloid was diluted to 10 mg Fe/mL and filtered easily and promptly through a 0.22 micron filter.

Filter sterilized superparamagnetic colloids made by any of the methods above can be injected into an animal (or human) at a dose of about 0.5–4 mg Fe/kg. It will accumulate in the liver and spleen and cause profound darkening of these tissues in MR imagers with T2 weighted pulse sequences. Results essentially those of FIG. 2 of U.S. Pat. 4,827,945 will be obtained, indicating the efficacy of these materials as MR contrast agents.

C. LACK OF ADVERSE REACTION EXHIBITED WHEN FILTER STERILIZATION REPLACES TERMINAL STERILIZATION FOR A SUPERPARAMAGNETIC IRON OXIDE COLLOID

A semiquantitative assay for the ability of various superparamagnetic iron oxide colloids to cause adverse reactions is given below. The decrease in an animal's blood pressure is monitored in response to injection of a compound, and taken as an indication of the ability of a compound to produce hypotension upon injection in humans.

A guinea pig (about 350 g) is anesthetized (sodium pentabarbital 35 mg/kg). The jugular vein and carotid artery were surgically exposed and cannulated with a tube filled with heparinized saline (10 IU/ml). The animal was placed in a small restrainer and permitted to awaken such that the corneal and startle reflexes were regained. The arterial cannula is connected to a arterial pressure transducer and then to recorder. A record of systolic and diastolic pressure is recorded for 20 minutes to establish the baseline values of the animal. Test solution is added via the jugular cannula at 1 mL/min and blood pressure recorded for 30 minutes. The lowest arterial blood pressure recorded with the initial 30 minutes after injection which was sustained for at least 1 minute is used to calculate the mean arterial blood pressure from baseline. The degree of change is graded as follows: no change (0): 0–15% decrease; mild (+): 16–20% decrease; moderate (++): 31–45% decrease and severe (+++): >45% decrease.

Table 1 shows the hemodynamic response resulting from superparamagnetic colloids that have been subjected to heat sterilization on the one hand, or filter sterilization on the other. The superparamagnetic iron oxide colloid used was prepared according to example 7.10 of U.S. Pat. No. 4,827,945 and then subjected to either terminal sterilization or filter sterilization. Terminal sterilization was achieved by autoclaving in the presence of citrate, as described in '945. Toxicological studies suggested the terminally sterilized, citrate stabilized colloid was a highly safe colloid, as indicated by its $LD_{50}$ of at least 3000 μmoles Fe/kg, as well as additional toxicity studies (see Weissleder et al. Amer. J. Roent. 152: 167–173 (1989)). The colloid has been judged sufficiently safe by the US Food and Drug Administration to permit human clinical trials.

Filter sterilization of the superparamagnetic iron oxide colloid obtained after ultrafiltration was achieved by using centrifugation before 0.22 micron filtration as described in Example 3. The hemodynamic response that is observed with terminally sterilized and filter sterilized colloids is compared in Table 1. Blood pressure responses from 5 guinea pigs are presented.

It can be seen that the terminally sterilized superparamagnetic colloid produced a far greater degree of blood pressure drop than could be obtained when heat stress was avoided, i.e., when filter sterilization was used. Based on Table 1, the filter sterilized superparamagnetic colloid would be expected to have a lower incidence of hypotensive responses when administered to a human population, than the terminally sterilized colloid.

Terminally sterilized dextran magnetite prepared in accordance with U.S. Pat. No. 4,101,435 has been studied by us for adverse reaction in the same manner as the terminally sterilized colloid that is reported in Table 1. Surprisingly, despite a relatively high $LD_{50}$ of 4100 mg Fe/Kg of body weight associated with this material, we found adverse reactions comparable to those for the terminally sterilized composition reported in Table 1. In view of these results and those of Table 1, we expect filter-sterilized dextran magnetite, prepared in a manner that avoids subjecting the active ingredient to heat stress, to result in a substantially reduced adverse reaction in comparison to the reaction from the terminally sterilized composition.

Table 1 should not be taken as precluding of the use of terminally sterilized superparamagnetic colloids as parenterally administered pharmaceuticals, or even as precluding the use of the particular terminally sterilized colloid involved in that study. With the terminally sterilized colloid of Table 1, a dose of 5–30 μmoles Fe/kg is sufficient to enhance MR images, while the dose used to produce hemodynamic changes is 400 μmoles Fe/kg. The terminally sterilized colloid of Table 1 may prove to have an incidence of adverse reactions at the dose selected as efficacious that is fully acceptable. In addition, terminal sterilization can still be preferred based on the higher degree of sterility assurance it provides. However, based on Table 1, the filter sterilized version of the colloid would be expected to have a lower incidence of hypotensive reactions in humans than the terminally sterilized colloid.

TABLE 1

Hemodynamic Response to Superparamagnetic Colloids Subjected to Terminal and Filter Sterilization

| Sterilization | Dose | Grade of Response |
|---|---|---|
| Terminal | 400 | +++ |
| Terminal | 400 | ++ |
| Filter | 800 | 0 |
| Filter | 4000 | 0 |
| Filter | 8000 | 0 |

Dose is in μmoles Fe/kg. Grade of response represents the degree of blood pressure drop measured as described above.

D. PRESERVATION OF SUPERPARAMAGNETIC IRON OXIDE COLLOID

The compositions prepared in accordance with the invention may be used immediately or further processed to enhance shelf life, i.e., to preserve potency and retard the growth of microorganisms. The simplest approach is to place the composition under refrigeration, however refrigeration may not provide a totally bacteriostatic environment.

When parenteral products of superparamagnetic iron oxide colloids are manufactured, they provide an extremely hospitable media for microbial growth. The active ingredient provides a source of iron; the lack of iron can limit the growth of microorganisms in many instances. Carbohydrates or proteins may be present, either as a coating from the colloid or as excipients. A source of nitrogen can be provided by traces of ammonia used to neutralize the iron salts during manufacture. An aqueous medium at near neutral pH is provided, so the colloid will not irritate upon injection. The problem of detecting microbial growth is complicated by the fact that the dark brown color of the colloidal iron oxide does not permit a visual inspection to observe microbial colonies, as is the case with noncolored parenterals. Thus, while filter sterilization produces materials which yield far less hemodynamic response (Table 1), the risk of microbial growth and the inability to detect that growth are shortcomings of the use of filter sterilization of these products.

One common solution to the problem of microbial growth in pharmaceutical products is the use of preservatives. Common preservatives include phenol, benzyl alcohol and thimerisol, as discussed in: M. J. Akers, Pharm. Tech., "Considerations in Selecting Antimicrobial Preservative Agents for Parenteral Product Development," May, 1984. A major complication from the use of preservatives is the possible interaction of the preservative with the active ingredient (superparamagnetic iron oxide colloid) over time. This can result in chemical changes of either the preservative or the colloid. In addition, the injection of the preservative itself may produce physiological effects which may compromise the safety or efficacy of the active ingredient. Therefore, if used, preservatives must be selected which do not reduce the effectiveness of the composition or create potential adverse reactions themselves.

Another alternative is lyophilization of the composition, which is later reconstituted with a suitable aqueous composition (such as saline solution) at the time of use. Surprisingly, we have found that under certain conditions the reconstituted product maintains the properties of the original composition. We have found, in particular, that lyophilization may be satisfactorily achieved if the composition includes a carbohydrate polymer such as dextran or sodium citrate or a combination thereof.

EXAMPLE 4: PRESERVATION OF FILTER STERILIZED SUPERPARAMAGNETIC IRON OXIDE COLLOID BY LYOPHILIZATION

Lyophilization offers a means of producing a bacteriostatic environment while avoiding the use of preservatives. Lyophilized powders with moisture contents below about 2% are considered bacteriostatic. Thus, by lyophilizing the filter sterilized colloid, the dangers of microbial growth during storage are eliminated. For superparamagnetic iron oxide colloids, lyophilization preserves the advantage gained by filter sterilization, namely, the lack of hemodynamic response, and minimizes the principle disadvantage of filter sterilization, namely, the risk of contamination in bottling attributable to various sources including air borne contamination.

However, lyophilization of particles and colloids is often accompanied by aggregation between the particles or colloids, which is seen as an increase in the particle or colloid size. For example, in the production of silanized magnetic particles, a dehydration step is used to bond the silane to the iron oxide surface. This is accomplished by adding a slurry of particles to glycerol and heating to drive off water. Air drying was avoided because of the tendency of particles to aggregate (see column 13, lines 16–33, USP 4,554,088 and column 17, lines 15–35, USP 4,827,945). We have found that the addition of excipients such as sodium citrate, dextran T-10 or dextran T-1, reduces or eliminates the tendency of superparamagnetic iron oxide colloids to aggregate during the lyophilization process.

The lyophilization of filter sterilized superparamagnetic iron oxide colloids utilizes a freezing step, a primary drying step and a secondary drying step. These are the three standard steps of pharmaceutical lyophilizations (see Williams, N.A. and Polli, G.P., J. parenteral Science and Technology, 38:48–59; 1984.) An example of a satisfactory lyophilization cycle is given below.

For the freezing step, 10 mL of colloid made according to example 1 is placed in a glass bottle. The colloid consists of 20 mg Fe/mL, with 30 mg/mL dextran T-10 and 10 mM sodium citrate added as excipients. The colloid is then placed in a freeze-drying apparatus, with the shelf temperature set for between $-40°$ C. and $-50°$ C. After 8 hours, the colloid reaches the shelf temperature, i.e. is frozen.

For the primary drying step, the vacuum is turned to a maximal setting, and the shelf temperature allowed to rise to $0°$ C. for 48 hours. The vacuum falls during primary drying, with a final value of less than about 100 microns being attained.

For the secondary drying step, the vacuum is maintained and the shelf temperature increased to $+20°$ C. for 24 hours.

As a result of lyophilization, a porous, hydophilic matrix is formed, with a volume equal to that of the original colloid, 10 mL. The matrix dissolves readily with water, saline, dextrose or other physiological fluid.

Figure 2:
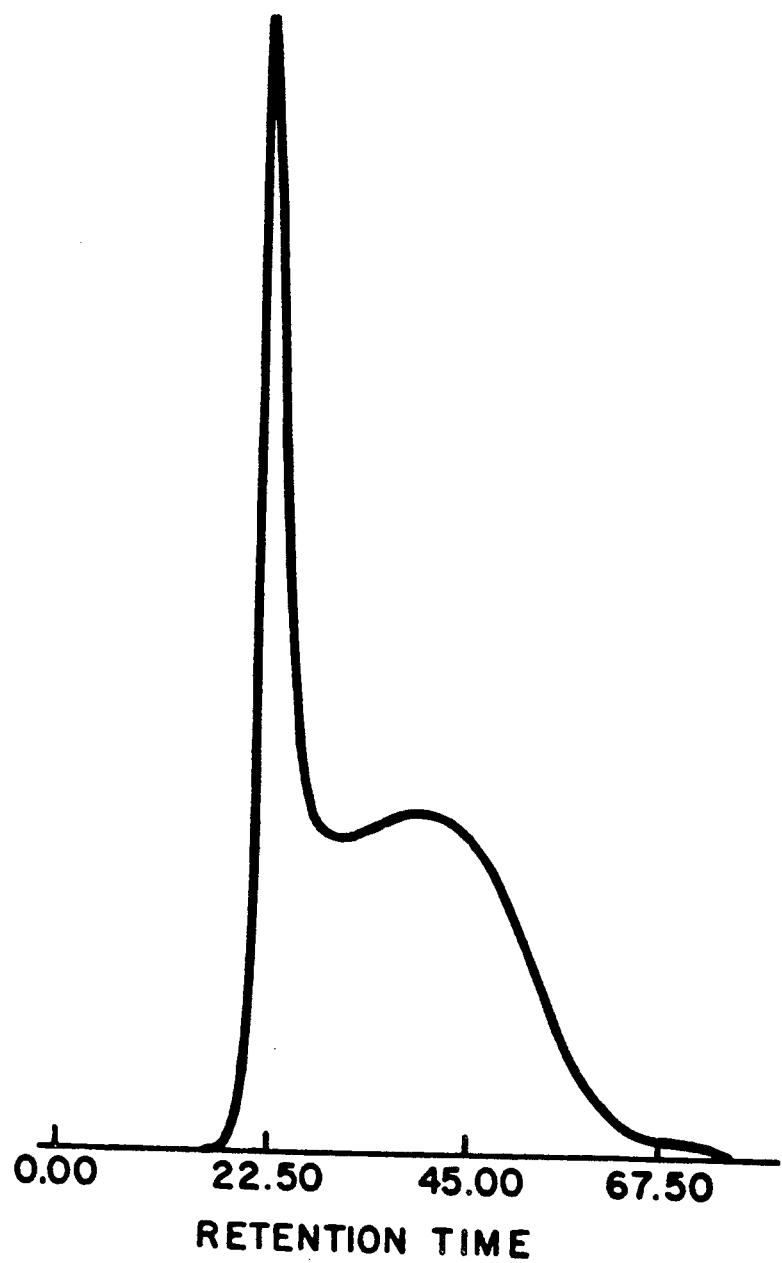
FIG. 2 is a Sepharose 4B chromatogram of superparamagnetic iron oxide colloid, lyophilized at 5.6 mg Fe/mL and 50 mM citrate, in accordance with Example 4.
Figure 3:
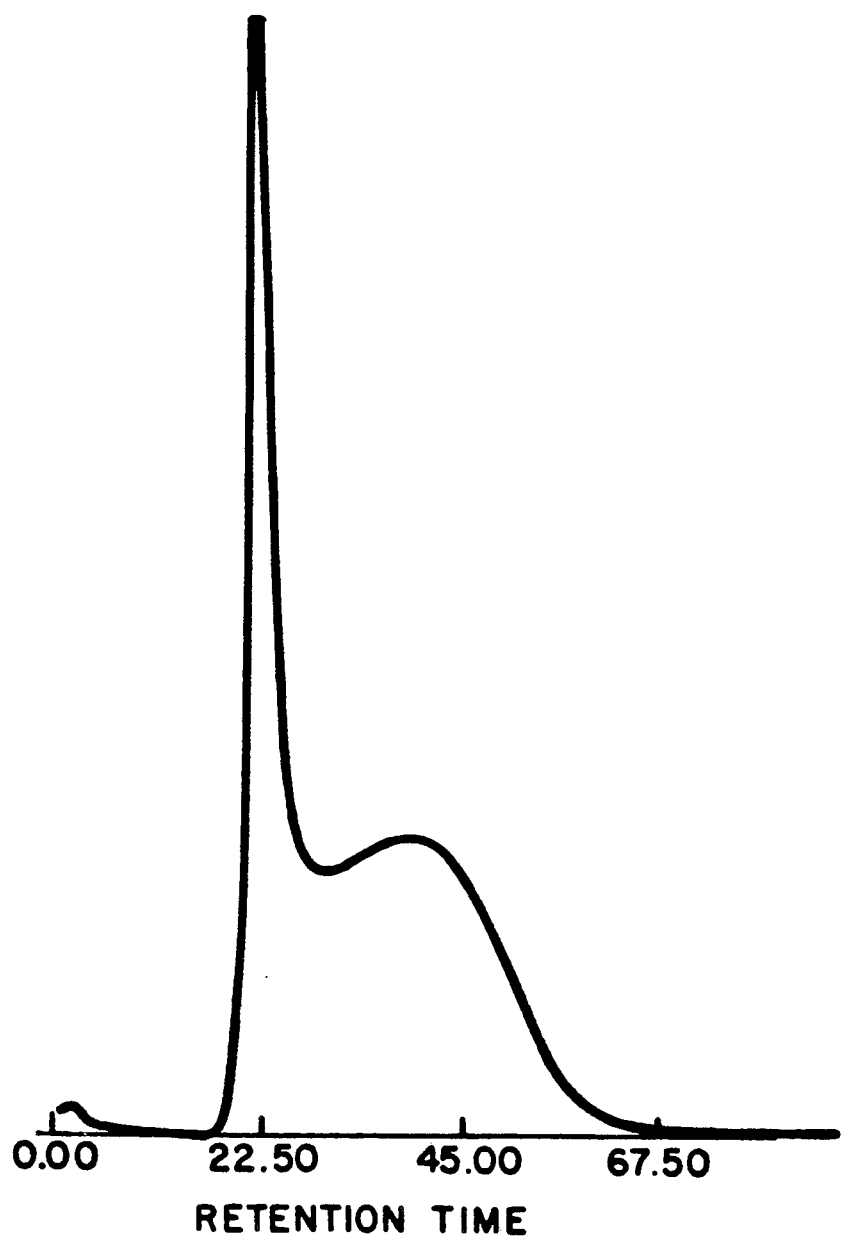
FIG. 3 is a Sepharose 4B chromatogram of superparamagnetic iron oxide colloid, lyophilized at 3.73 mg Fe/mL in 26.7 mg/mL dextran T-10, in accordance with Example 4.

FIGS. 1-3 show the effects of lyophilization on the size distribution of a superparamagnetic iron oxide colloid made according to Example 3 of this application or 7.10 of USP 4,827,945. The size distribution of superparamagnetic iron oxide colloids may be measured by gel filtration on Sepharose 4B; the chromatograms shown below may be compared with others for the same material (See FIG. 4 of Josephson, et al., Magnetic Resonance Imaging 8:637–646; 1990). FIG. 1 shows the colloid before lyophilization. In FIG. 2, the colloid (5.6 mg Fe/mL or 100 mM) was lyophilized in 50 mM citrate. In FIG. 3, the colloid (3.73 mg Fe/mL or 66.8 mM) was lyophilized in 26.7 mg/ml dextran T-10. All three chromatograms are similar, showing the size distribution of the colloid was unchanged upon lyophilization.

Depending on the superparamagnetic iron oxide colloid used and the conditions of lyophilization, failure to add any of the colloid stabilizing excipients mentioned above may result in unwanted changes. These changes include: (i) an increase in the area of the large peak relative to the small peak on chromatography; and (ii) an increase in the level of particulates seen upon filtration. Particulates are measured by counting, with the aid of a microscope, the number of particles retained by a 0.8 micron filter.

Superparamagnetic iron oxide colloids may be lyophilized when iron concentrations are between about 0.5 and 40 mg/mL, when dextran is present as an excipient between 0.3 and 10 mg dextran per mg of iron, and when citrate is present as an excipient between 10 mM citrate per 1000 mM of iron and 500 mM citrate per 1000 mM iron. Either excipient may be used alone or in combination to stabilize the colloidal products for the lyophilization process. Some examples of colloidal formulations are given below in Table 2. The dextran and citrate concentrations given are those added as excipients after synthesis of the active ingredient. Dextrans of molecular weights between 1,000 and 70,000 may be used. The citrate may be sodium or ammonium citrate. The pH of the colloid is between 6.5 and 9.0 before lyophilization. As described above, the composition after lyophilization in the manner described is typically a solid hydrophilic matrix that is readily reconstituted in water, saline, dextrose, or other aqueous physiological solutions. (The term "colloid" used herein and in the accompanying claims includes the solid lyophilized composition as well as liquid dispersions.) If an excipient is being used, it is important that the excipient be a composition that is compatible with the colloid. The excipient preferably is of low toxicity, has a history of pharmaceutical use, is lyophilizable and prevents unwanted physical changes in the colloid. The foregoing dextrans and citrates are suitable, but other compositions are possible, such as hydroxyethyl starches.

TABLE 2

Some Excipient and Iron concentrations for
Lyophilization of Superparamagnetic Iron Oxide Colloids

| Iron (mM) | Iron (mg/mL) | Citrate (mM) | Dextran (mg/mL) |
|---|---|---|---|
| 357 | 20 | 10 | 30 |
| 357 | 20 | 20 | 30 |
| 100 | 5.6 | 50 | 0 |
| 66.8 | 3.73 | 0 | 26.7 |
| 8.9 | 0.5 | 10 | 10 |
| 661 | 37 | 10 | 40 |

What is claimed is:

1. An improved method, for obtaining an in vivo MR image of an organ or tissue of an animal or human subject, of the type including administering to such subject as a contrast agent to enhance such MR image an effective amount of a colloid including superparamagnetic metal oxide particles dispersed in a physiologically acceptable carrier, in such a manner as to provide a reduction in toxicity in comparison with that associated with administration of the colloid after terminal sterilization, wherein the improvement comprises preparing and sterilizing the colloid in a manner that avoids subjecting the resulting active ingredient to heat stress.

2. A method according to claim 1, wherein preparing and sterilizing the colloid includes the step of sterilizing the colloid by filtration.

3. A method according to claim 2, wherein the step of sterilizing the colloid by filtration includes the step of removing materials from the colloid that would otherwise clog the filter used to achieve sterilization.

4. A method according to claim 3, wherein the step of sterilizing the colloid by filtration includes passing the colloid through successively smaller pore size filters, the smallest pore size filter being not greater than approximately 220 nm.

5. A method according to claim 3, wherein the step of sterilizing the colloid by filtration includes using a magnetic filter to selectively remove larger particles.

6. A method according to claim 3, wherein the step of sterilizing the colloid by filtration includes using column chromatography to selectively remove larger particles from the colloid.

7. A method according to claim 3, wherein the step of sterilizing the colloid by filtration includes centrifuging the colloid and passing the supernatant through a filter having a pore size not greater than approximately 220 nm.

8. A method according to claim 1, wherein the metal oxide particles comprise crystals, each crystal about 10 to about 500 angstroms in diameter and having an overall diameter of about 10 to not more than about 4000 angstroms as measured to light scattering.

9. A method according to claim 2, wherein the metal oxide particles comprise crystals, each crystal about 10 to about 500 angstroms in diameter and having an overall diameter of about 10 to not more than about 4000 angstroms as measured to light scattering.

10. A method according to claim 3, wherein the metal oxide particles comprise crystals, each crystal about 10 to about 500 angstroms in diameter and having an overall diameter of about 10 to not more than about 4000 angstroms as measured to light scattering.

11. A method according to claim 1, wherein the metal oxide particles are associated with a macromolecular substance.

12. A method according to claim 2, wherein the metal oxide particles are associated with a macromolecular substance.

13. A method according to claim 3, wherein the metal oxide particles are associated with a macromolecular substance.

14. A method according to claim 1, wherein the colloid includes dextran magnetite.

15. A method according to claim 2, wherein the colloid includes dextran magnetite.

16. A method according to claim 3, wherein the colloid includes dextran magnetite.

17. A method according to claim 2, further comprising lyophilizing the filter-sterilized colloid.

18. A method according to claim 17, wherein the filter-sterilized colloid is lyophilized in the presence of a compatible excipient.

19. A method according to claim 18, wherein the excipient includes one or more compositions selected from the group consisting of a dextran and a citrate anion.

20. A method according to claim 19, further comprising reconstituting the lyophilized colloid with an aqueous composition.

* * * * *